(12) United States Patent
Saptharishi

(10) Patent No.: US 10,978,190 B2
(45) Date of Patent: Apr. 13, 2021

(54) SYSTEM AND METHOD FOR VIEWING MEDICAL IMAGE

(71) Applicant: KONINKLIJKE PHILIPS N.V., Eindhoven (NL)

(72) Inventor: Ramkumar Saptharishi, Solon, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 151 days.

(21) Appl. No.: 16/303,919

(22) PCT Filed: Jun. 16, 2017

(86) PCT No.: PCT/EP2017/064792
§ 371 (c)(1),
(2) Date: Nov. 21, 2018

(87) PCT Pub. No.: WO2017/216356
PCT Pub. Date: Dec. 21, 2017

(65) Prior Publication Data
US 2020/0321098 A1    Oct. 8, 2020

Related U.S. Application Data

(60) Provisional application No. 62/350,761, filed on Jun. 16, 2016.

(51) Int. Cl.
*G16H 30/20* (2018.01)
*G16H 15/00* (2018.01)
(Continued)

(52) U.S. Cl.
CPC .......... *G16H 10/60* (2018.01); *G06T 7/0012* (2013.01); *G06T 7/11* (2017.01); *G16H 15/00* (2018.01); *G16H 30/20* (2018.01); *G16H 30/40* (2018.01); *G16H 40/67* (2018.01); *G16H 50/20* (2018.01); *G06T 2207/30004* (2013.01)

(58) Field of Classification Search
CPC ........ G16H 30/20; G16H 40/67; G16H 10/60; G16H 15/00; G16H 50/20; G16H 30/40; G06T 7/11; G06T 7/0012; G06T 2207/30004
See application file for complete search history.

(56) References Cited

U.S. PATENT DOCUMENTS 8,976,190 B1 *  3/2015  Westerhoff ............ G06F 19/321
                                                    345/581
9,654,739 B1 *  5/2017  Mitchell ............... H04N 5/2228
(Continued)

FOREIGN PATENT DOCUMENTS

JP    2013114485 A    6/2013
WO   2010035167 A1   4/2010
(Continued)

*Primary Examiner* — David F Dunphy

(57) ABSTRACT

A system for enabling an automatic image viewing workflow, includes a patient medical data interface (120) for obtaining medical data of a patient; one or more image viewing subsystems (180); a processing subsystem (160) configured to extract context specific data from the patient medical data, and initiate at least one medical image viewing subsystems (180) based on the extracted context specific data.

16 Claims, 7 Drawing Sheets

(51) Int. Cl.
*G16H 10/60* (2018.01)
*G16H 30/40* (2018.01)
*G16H 50/20* (2018.01)
*G16H 40/67* (2018.01)
*G06T 7/11* (2017.01)
*G06T 7/00* (2017.01)

(56) References Cited

U.S. PATENT DOCUMENTS

2012/0183191 A1 7/2012 Nakamura
2013/0129198 A1 5/2013 Sherman et al.

FOREIGN PATENT DOCUMENTS

WO 2011132097 A2 10/2011
WO 2015183753 A1 12/2015

* cited by examiner

| Z-axis 510 | # Beds 520 | Isotope 530 | Exam Card Attribute or DICOM tag Attribute 540 | Key Word in Medical Report or Audio 550 | Patient Coordinate based on 1 Bed, Z-axis (Body Segment) 560 | Image viewing subsystems 570 | Weight Factor assigned to each image viewing subsystem 580 | Decision/Result of the most suitable image viewing subsystem 590 | Weight Factor Decision/Result - PET/CT or CT 600 |
|---|---|---|---|---|---|---|---|---|---|
| 150cm | 8 | FDG | Body | | | Oncology Cardiology Neurology | 0.8 0.1 0.1 | Oncology | PET/CT - 1.0 CT: 0.0 |
| | | | Perfusion | | | Oncology Cardiology Neurology | 0.1 0.8 0.1 | Cardiology | PET/CT - 1.0 CT: 0.0 |
| | | | Viability | | | Oncology Cardiology Neurology | 0.1 0.8 0.1 | Cardiology | PET/CT - 1.0 CT: 0.0 |
| | | | Perfusion + Head | | | Oncology Cardiology Neurology | 0.1 0.1 0.8 | Neurology | PET/CT - 1.0 CT: 0.0 |
| | | Ammonia | | | | Oncology Cardiology Neurology | 0.0 1.0 0.0 | Cardiology | PET/CT - 1.0 CT: 0.0 |
| | | F18-Dopamine 531 | | | | Oncology Cardiology Neurology | 0.0 0.0 1.0 | Neurology 591 | PET/CT - 1.0 CT: 0.0 |
| 20cm | | F18-Dopamine | | | | Oncology Cardiology Neurology | 0.0 0.0 1.0 | Neurology | PET/CT - 1.0 CT: 0.0 |
| 20cm | | Ammonia | | | | Oncology Cardiology Neurology | 0.1 0.8 0.1 | Cardiology | PET/CT - 1.0 CT: 0.0 |
| 20cm | | | Head | | | Oncology Cardiology Neurology | 0.1 0.1 0.8 | Neurology | PET/CT - 1.0 CT: 0.0 |

Fig. 5a

| Z-axis 510 | # Beds 520 | Isotope 530 | Exam Card Attribute or DICOM tag Attribute 540 | Key Word in Medical Report or Audio 550 | Patient Coordinate based on 1 Bed, Z-axis (Body Segment) 560 | Image viewing subsystems 570 | Weight Factor (From Algorithm) 580 | Decision/Result 590 | Weight Factor Decision/Result - PET/CT or CT 600 |
|---|---|---|---|---|---|---|---|---|---|
| 20cm | | | ECG | | | Oncology<br>Cardiology<br>Neurology | 0.1<br>0.8<br>0.1 | Cardiology | PET/CT - 1.0<br>CT: 0.0 |
| | 8 | | | | | Oncology<br>Cardiology<br>Neurology | 0.8<br>0.1<br>0.1 | Oncology | PET/CT - 1.0<br>CT: 0.0 |
| | 2 | Ammonia | | | | Oncology<br>Cardiology<br>Neurology | 0.1<br>0.8<br>0.1 | Cardiology | PET/CT - 1.0<br>CT: 0.0 |
| | | | | Brain Tumor | | Oncology<br>Cardiology<br>Neurology | 0.1<br>0.1<br>0.8 | Neurology | PET/CT - 1.0<br>CT: 0.0 |
| | | | | Bone | | Oncology<br>Cardiology<br>Neurology | 0.8<br>0.1<br>0.1 | Oncology | PET/CT - 1.0<br>CT: 0.0 |
| | | | | Lymphoma | | Oncology<br>Cardiology<br>Neurology | 0.8<br>0.1<br>0.1 | Oncology | PET/CT - 1.0<br>CT: 0.0 |
| | | | Image Processing Filter Type: cardiac | | | Oncology<br>Cardiology<br>Neurology | 0.1<br>0.8<br>0.1 | Cardiology | PET/CT - 1.0<br>CT: 0.0 |
| | | | | myocardial | | Oncology<br>Cardiology<br>Neurology | 0.1<br>0.8<br>0.1 | Cardiology | PET/CT - 1.0<br>CT: 0.0 |
| | 1 | | | Alzhimer | 20 cm | Oncology<br>Cardiology<br>Neurology | 0.0<br>0.0<br>1.0 | Neurology | PET/CT - 1.0<br>CT: 0.0 |

Fig. 5b

| Z-axis | # Beds | Isotope | Exam Card Attribute or DICOM tag Attribute | Key Word in Medical Report or Audio | Patient Coordinate based on 1 Bed, Z-axis (Body Segment) | Image viewing subsystems | Weight Factor (From Algorithm) | Decision/Result | Weight Factor Decision/Result - PET/CT or CT |
|---|---|---|---|---|---|---|---|---|---|
| 510 | 520 | 530 | 540 | 550 | 560 | 570 | 580 | 590 | 600 |
| | 1 | | | myocardial | 50cm | Oncology Cardiology Neurology | 0.0 1.0 0.0 | Cardiology | PET/CT - 1.0 CT: 0.0 |
| | 8 | | | Lymphoma | Whole Body | Oncology Cardiology Neurology | 1.0 0.0 0.0 | Oncology | PET/CT - 1.0 CT: 0.0 |
| | 1 | | Brain | | | Oncology Cardiology Neurology | 0.0 0.0 1.0 | Neurology | PET/CT - 1.0 CT: 0.0 |
| | 1 | | Cardiac | | | Oncology Cardiology Neurology | 0.0 1.0 0.0 | Cardiology | PET/CT - 1.0 CT: 0.0 |
| 150 | 8 | FDG | Body | Lymphoma | Whole Body | Oncology Cardiology Neurology | 1.0 0.0 0.0 | Oncology | PET/CT - 1.0 CT: 0.0 |
| 20 | 1 | FDG | Cardiac | Viability | Cardiac | Oncology Cardiology Neurology | 0.0 1.0 0.0 | Cardiology | PET/CT - 1.0 CT: 0.0 |
| 20 | 1 | FDG | Neuro | Alzhimer | Brain | Oncology Cardiology Neurology | 0.0 0.0 1.0 | Neurology | PET/CT - 1.0 CT: 0.0 |
| None | None | None | Neuro | Alzhimer | Brain | Oncology Cardiology Neurology | 0.0 0.0 1.0 | Neurology | CT - 1.0 PET/CT - 0.0 |
| | | | | Follow up | Follow up | Use the knowledge of the prior exam attribute to open up the application automatically. | | | |

Fig. 5c

SYSTEM AND METHOD FOR VIEWING MEDICAL IMAGE

This application is the U.S. National Phase application under 35 U.S.C. § 371 of International Application No. PCT/EP2017/064792, filed on Jun. 16, 2017, which claims the benefit of Provisional Application Ser. No. 62/350,761, filed Jun. 16, 2016. These applications are hereby incorporated by reference herein.

FIELD OF THE INVENTION

The invention relates to a system and a method for enabling an automatic medical image viewing workflow.

The invention further relates to workstation or image apparatus comprising the system. The invention further relates to a computer program product comprising instructions for causing a processor system to perform the method.

BACKGROUND OF THE INVENTION

Current workflow of viewing medical images utilizes various types of medical image viewing applications such as oncology, cardiology or neurology related medical image viewing applications executing on a professional image visualization platform which requires substantive user interaction.

In addition, it is very common that prior knowledge of the acquired medical image data is not available when selecting the most suitable medical image viewing application to view such acquired medical image. Therefore, in the current workflow, the user may have to open up more than one medical image viewing application to verify which medical image viewing application is the most suitable one despite any prior knowledge of the acquired medical image data, which is time consuming and may lead to incorrect view result.

SUMMARY OF THE INVENTION

There may therefore be a need in the art for an improved method and/or related system to address at least some of the deficiencies noted above.

A first aspect of the inventions provides a system for enabling an automatic medical image viewing workflow, comprising:
 a patient medical data interface for obtaining medical data of a patient;
 one or more medical image viewing subsystems; a processing subsystem configured to extracting context specific data from the patient medical data, and initiating at least one medical image viewing subsystems based on the extracted context specific data.

A further aspect of the invention provides a workstation or imaging apparatus comprising the system.

A further aspect of the invention provides a network system comprising the system, and a remote device in communicative with the system, wherein the remote device comprises one or more medical image viewing subsystems, and wherein the processing subsystem is configured to initiate one or more medical image viewing subsystems based on the extracted context specific data.

A further aspect of the invention provides a method of enabling an automatic medical image viewing workflow, comprising:

obtaining medical data of a patient;
 extracting context specific data from the patient medical data;
 deriving a predefined rule engine database comprising association between the context specific data and one or more medical image viewing subsystems; and
 initiating at least one medical image viewing subsystem by comparing the context specific data with the predefined rule engine database.

A further aspect of the invention provides a computer program product comprising instructions to cause a processing subsystem to perform the method. The medical image data of a patient may contain medical image acquired from various imaging modalities, including but not limited to Ultrasound, Computed Tomography (CT), Positron emission tomographycomputed tomography (PET/CT), Magnetic Resonance (MR) imaging, etc. Furthermore, the medical data of a patient may also include any relevant data associated with such acquired medical image data. By automatically initiating at least one medical image viewing subsystem based on the context specific data extracted from the patient medical data, an improved workflow of viewing medical images with minimum user interaction is achieved.

In an embodiment, the patient medical data comprises one or more of the following:
 medical image of the patient, such as a segmented medical image;
 medical image protocol associated with the medical image of the patient, such as DICOM tag;
 audio data associated with the medical image of the patient;
 medical exam card or medical report/record associated with the medical image of the patient.

In an embodiment, the processing subsystem is configured to extract context specific data from the medical image indicating the location of the segmented medical image with respect to the whole body of the patient.

In an embodiment, the processing subsystem is configured to extract key attributes from the medical image protocol inferring the relevant image viewing subsystem to be initiated.

In an embodiment, the processing subsystem is configured to extract keywords from the audio data inferring the relevant image viewing subsystem to be initiated.

In an embodiment, the processing subsystem is configured to extract keywords from the medical exam card or medical report inferring the relevant image viewing subsystem to be initiated, such as the size of field of view, the organ specific radio-isotopes used during isotopes used, or any combination thereof.

In an embodiment, the system further comprises a memory subsystem configured for storing a predefined rule engine database comprising association between the context specific data and the one or more medical image viewing subsystems; wherein the processing subsystem is configured to initiate one or more medical image viewing subsystems by comparing the context specific data with the predefined rule engine database.

In an embodiment, the memory subsystem is further configured to store a learn model associated with the initiation of the one or more medical image viewing subsystems to determine whether the initialized one or more medical image viewing subsystem is applicable to a user of the system.

In an embodiment, the processing subsystem is further configured for
 receiving feedback information from the user input interface indicating the correctness of the medical image viewing subsystem with respect to the patient medical data and the extracted context specific data;

updating the rule engine database based on the received feedback information from the user input interface;

retraining the learn model based on the updated rule engine database using a machine learning process.

Advantageously, this may allow an automatically update of the rule engine database to be adapted such that the precision of the determination of the most suitable medical image viewing subsystem for a specific medical image can be improved.

In an embodiment, the rule engine database further comprises a list of links, wherein each link includes an association between a specific image viewing subsystem and an image acquisition device.

In an embodiment, the system further comprises a user input interface for enabling a user to:

provide feedback information to the processing subsystem;

modify the rule engine database; or modify the patient medical data, such as DICOM tag.

In an embodiment, the processing subsystem may initiate one or more medical image viewing subsystems based on the correlation of the different types of context specific data. Advantageously, by initiating one or more medical image viewing subsystems based on the correlation of the different types of context specific data, the precision of the determination of the most suitable medical image viewing subsystem for a specific medical image can be improved.

BRIEF DESCRIPTION OF THE DRAWINGS

These and other aspects of the invention will be apparent from and elucidated further with reference to the embodiments described by way of example in the following description and with reference to the accompanying drawings, in which

FIGS. 5a-5c show examples of a rule engine database according to an embodiment of the invention.

It should be noted that the figures are purely diagrammatic and not drawn to scale. In the Figures, elements which correspond to elements already described may have the same reference numerals.

DETAILED DESCRIPTION OF EMBODIMENTS

Figure 1:
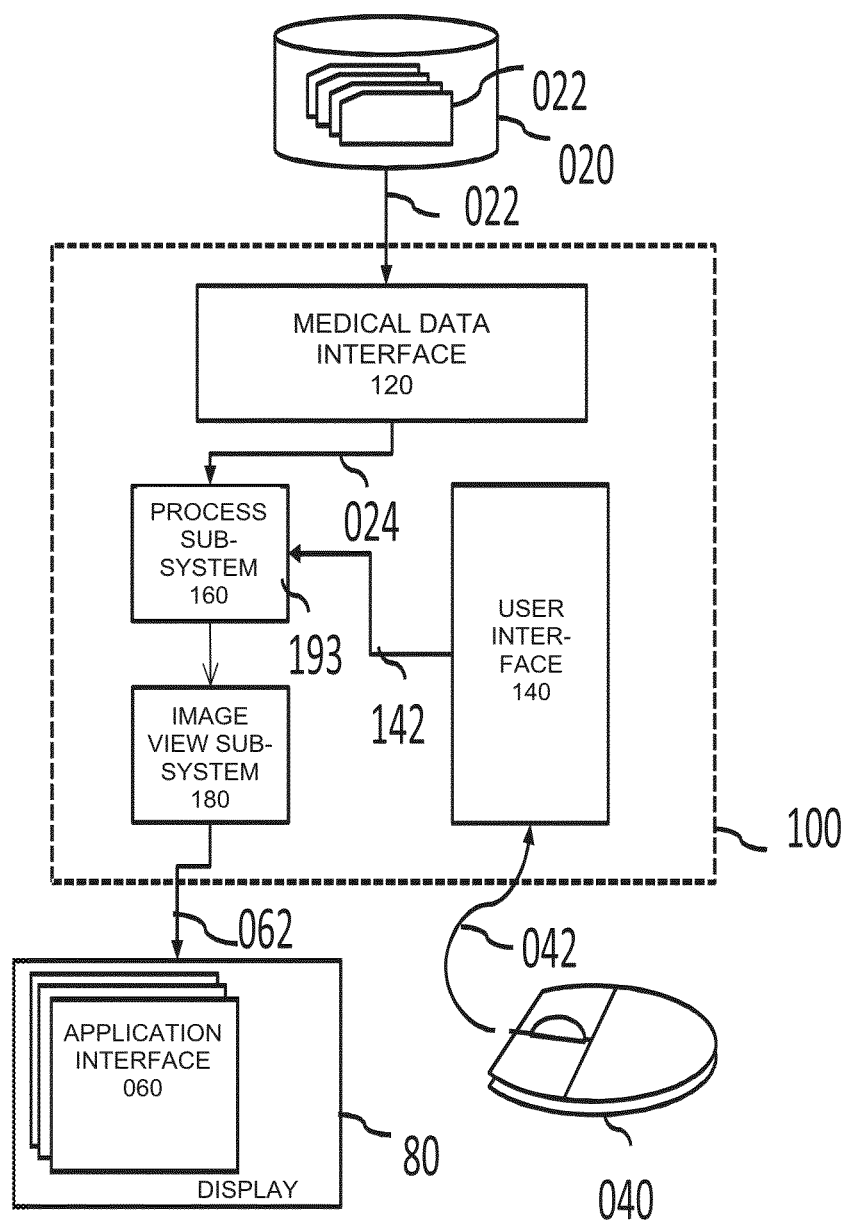
FIG. 1 shows a system for viewing medical image according to an embodiment of the invention.

It should be understood that the Figures are merely schematic and are not drawn to scale. It should also be understood that the same reference numerals are used throughout the Figures to indicate the same or similar parts.

In the context of the present application, a patient medical data means medical image data of a patient and/or any relevant data associated with such medical image data. More specifically, the patient medical data may comprise one or more of i) medical image of a patient, such as a segmented medical image; ii) medical image protocol associated with the medical image of the patient, such as a DICOM tag; iii) audio data associated with the medical image of the patient; iv) medical exam card or medical report/record associated with the medical image of the patient; and v) the patient ID.

In the context of the present application, a context specific data means any data that may infer the association between the medical image to be viewed and the most suitable image view subsystem for viewing such medical image.

In the context of the present application, an oncology, cardiology or neurology related medical image viewing application means a medical image viewing application having functionalities that are in particularly suitable for viewing oncology, cardiology or neurology related medical images. For instance, a cardiology related medical image viewing subsystem may have Dynamic Myocardial Perfusion (DMP) function for visualizing cardiac image focusing on the left ventricular myocardium that is specific to view cardiology related patient medical images. Alternatively, an oncology or neurology related image viewing subsystem may have Multi-Modality Tumor Tracking (MMTT) function for monitoring changes in disease status, or Neuro Perfusion (NP) function for viewing blood perfusion to the brain, that is specific to view oncology or neurology related patient medical images, respectively.

FIG. 1 shows a system 100 which is configured to enable an automatic image viewing. The system 100 comprises a patient medical data interface 120 for obtaining medical data of a patient. In the example of FIG. 1, the patient medical data interface 120 is shown to be connected to an external data repository 020 which comprises the medical data of a patient 022 including image data as well as other associated data of a patient. For example, the data repository 020 may be constituted by, or be part of, a Picture Archiving and Communication System (PACS) of a Hospital Information System (HIS) to which the system 100 may be connected or comprised in. Accordingly, the system 100 may obtain access to the medical data 022 of a patient such as medical images via the HIS. Alternatively, the medical data 022 of a patient may be accessed from an internal data storage of the system 100. In general, the patient medical data interface 120 may take various forms, such as a network interface to a local or wide area network, e.g., the Internet, a storage interface to internal data storage, external data storage, or a Cloud, etc. Alternatively, the external data repository 020 may be a RFID tag.

Furthermore, the system 100 is shown to comprise a user input interface 140 configured to receive user input commands 042 from a user input device 040 to enable the user to provide feedback information 142 to the system 100. The user input device 040 may take various forms, including but not limited to a computer mouse, touch screen, keyboard, etc. FIG. 1 shows the user input device to be a computer mouse 040. In general, the user input interface 140 may be of a type which corresponds to the type of user input device 040, i.e., it may be a thereto corresponding user device interface.

The system 100 may further comprise a memory subsystem 190 (not shown in FIG. 1) configured for storing a predefined rule engine database 193 comprising association between context specific data and the one or more medical image viewing subsystems 180 to be initialized. The memory subsystem 190 may also store the previously used medical image viewing subsystem 180 for a specific patient. Alternatively, the memory subsystem 190 and the predefined rule engine database 193 may be formed as part of the processing subsystem 160. Examples of said predefined rule engine database 193 can be found in FIGS. 5a-5c. Alternatively, the memory subsystem 190 may be either an internal part of the system 100 or an external part of the system 100. In an embodiment, the processing subsystem 160 may be configured to initiate one or more medical image viewing subsystems 180 by comparing the context specific data with the predefined rule engine database 193.

The system 100 is further shown to comprise a processing subsystem 160 configured to receive patient medical data 024 from the patient medical data interface 120. The processing subsystem 160 is further configured to extract context specific data from the received patient medical data 024, and initiate one or more medical image viewing subsystems 180 based on the extracted context specific data. Each image viewing subsystem 180 may have different functionalities that are in particularly suitable for a specific patient medical data (022, 024) such as medical images.

In an embodiment, the processing subsystem may extract context specific data from the medical image indicating the location of the segmented medical image with respect to the whole body of the patient. In an example, the process of acquiring the medical images of a whole body of a patient may be performed by dividing the whole body into multiple segments in which the head is in the top segment and the heart is in the upper middle segment, etc. The region of a patient from eyes to thigh will be acquired with multiple beds based on a predefined image acquisition plan. Here, the bed means the area of the body to be imaged by the detector field of view of an image acquisition device. For instance, the PET detector field of view is typically 15 cm. In order to derive an oncology related medical image of the whole body, the detector field of view has to move over the patient anatomy by moving the table. This is typically referred as "multiple bed" imaging. Each derived segmented image may contain Z-axis coordinate indicating the portion of body in the segmented image with respect to the whole body of the patient. In an example, said Z-axis coordinates may be used as a context specific data. Examples can be found in column 510 of FIGS. 5a-5c. For instance, if Z-axis coordinate indicates that the portion of body in the segmented image relates to a brain of the patient, then it infers that the image viewing subsystem 180 having the neurology related functionalities may be the most suitable image view subsystem for viewing this segmented image. In another example, the Z-axis coordinates combined with the X-axis coordinates, Y-axis coordinates, and information of the number of beds may be used as a context specific data. Examples can be found in column 560 of FIGS. 5a-5c.

In an embodiment, the processing subsystem 160 may extract key attributes or specific data element from the medical image protocol in the patient medical data (022, 024) inferring the relevant image viewing subsystem 180 to be initiated. Here, the medical image protocol means any protocols or standards used in the medical image viewing, storing, printing, and transmitting information in medical image, such as the Digital Imaging and Communications in Medicine (DICOM) protocol, or Health Level Seven (HL7). In an example, the DICOM tag may contain key attributes such as "TomoClass", or "CardiacTriggerSequence" which may infer that the image viewing subsystem 180 having the oncology or cardiology related functionalities may be the most suitable image view subsystem for viewing such medical image. In an example, the user may insert additional key attributes to the DICOM tag to specify the association between the context specific data in the DICOM tag and the image viewing subsystem 180.

In an embodiment, the processing subsystem 160 may extract keywords from the audio data included in the patient medical data (022, 024) which may infer the relevant image viewing subsystem to be initiated. The audio data may be attached in the medical report of the patient, or may be created by the medical professionals, such as dictation when generating the associated medical image. In an example, the processing subsystem 160 may directly extract keywords from the audio data by well-known technology, such as the technology disclosed in Armando Muscariello et. al. AUDIO KEYWORD EXTRACTION BY UNSUPERVISED WORD DISCOVERY in "INTERSPEECH 2009: $10^{th}$ Annual conference of the International Speech Communication Association 2009". The extracted keywords may include, e.g., "brain", "tumor" inferring that the neurology related image viewing subsystem 180 would be the most suitable image viewing subsystem. In another example, the processing subsystem 160 may trigger an audio data analysis subsystem 197 (not shown in FIG. 1) to extract and analyze the keywords form the audio data. The audio data analysis subsystem 197 may extract the keywords in the same way as mentioned above, and compare the keywords with a predefined rule engine database 193. The predefined rule engine database 193 may include information indicating the association between the audio data keywords and the one or more image viewing subsystems 180. Examples can be found in column 550 and column 590 of FIGS. 5a-5c. Based on the comparison, the audio data analysis subsystem 197 may trigger the initiation of the specific medical image viewing subsystems 180 according to the rule engine database 193.

In an embodiment, the processing subsystem 160 may extract keywords from the medical exam card, electronic medical records or medical report included in the patient medical data (022, 024) inferring the relevant image viewing subsystem 180 to be initiated, such as the size of Field of View (FOV), the organ specific radio-isotopes used during isotopes used, or any combination thereof. Here, the medical exam card means the set of data acquisition and imaging parameters or a clinical protocol template. In an example, if the extracted keywords indicate that the prescribed radioactive isotope is $^{18}$F-Fluoro-deoxy-glucose (FDG) and the prescribed FOV is greater than 150 cm, then it infers that the medical image viewing subsystem 180 having the oncology related functionalities may be the most suitable image view subsystem for viewing such medical image. Alternatively, if the extracted keywords indicate that the prescribed isotope is FDG and the prescribed FOV is about 20 cm, then it infers that the image viewing subsystem 180 having the cardiology related functionalities may be the most suitable image view subsystem for viewing such medical image.

In an embodiment, the processing subsystem 160 may extract more than one type of context specific data, such as the keywords of audio data, the keywords of medical report, the key attributes of DICOM tag, and may determine which image viewing subsystem 180 to be initialized based on the correlation of the different types of context specific data as defined in the rule engine database 193. A predefined weight factor may be assigned to each type of context specific data and a decision tree may be used in the determination of the correlation of the different types of context specific data. Examples can be found in column 580 of FIGS. 5a-5c. For instance, if the Isotope attribute is FDG, Number of beds selected is 1 or 2, the exam card or medical report had a "myocardial" attribute, then the processing subsystem 160 may determine that the cardiology related image viewing subsystem 180 is the most suitable image viewing subsystem to view such medical image based on the correlation in the rule engine database 193.

Each medical image viewing subsystems 180 is associated with an application interface 60. Once the one or more image viewing subsystem 180 is initiated by the processing subsystem 160, the corresponding application interface 60 is automatically displayed on a display 80 via a display signal 062 generated by the one or more image viewing subsystem 180. The processing subsystem 160 is shown to receive data 142 from the user input interface 140. Alternatively, the display 80 may be an internal part of the system 100. Alternatively, the display signal 062 may be generated directly by the processing subsystem 160. Alternatively, the patient medical interface 120 is configured to directly extract context specific data from the received patient medical data 022 and transmit the extracted context specific data to the processing subsystem 160.

In an embodiment, the rule engine database 193 may further comprise a list of links. Each link may include an association between a specific image viewing subsystem and an image acquisition device. For instance, the link may include an association between a CT device and an image viewing subsystem specific to CT device. The processing subsystem 160 may trigger an initiation of a medical image viewing subsystem 180 based on the link provided in the rule engine database 193. Examples can be shown in FIGS. 5a-5c. For instance, if the image acquisition device is PET/CT as shown in column 600, the corresponding medical image viewing subsystem may be cardiology related subsystem as shown in column 590.

The memory subsystem 190 may be further configured to store a learn model 195 associated with the initiation of the one or more medical image viewing subsystems 180 to determine whether the initialized one or more image viewing subsystem 180 is applicable to a user of the system 100. The processing subsystem 160 may further receive feedback information 142 from the user input interface 140 indicating the correctness of the image viewing subsystem 180 with respect to the patient medical data (022, 024) and the extracted context specific data. Accordingly, the processing subsystem 160 may update the rule engine database 193 based on the received feedback information 142 from the user input interface 140. Afterwards, the processing subsystem 160 may retrain the learn model 195 based on the updated rule engine database 193 using a machine learning process to verify whether the updated rule engine database 193 is correct or not. For instance, the machine learning process may be a logistic regression algorithm. In some embodiment, the learned model may be adapted to the particular user by receiving feedback information as to the use of a specific image acquisition device or the viewing of a specific patient medical image.

The operation of the system 100 may be briefly summarized as follows. The user input interface 140 is configured to allow the commencement of operating the system 100, e.g. by providing a start signal. The display processor 160 is configured to, during operation of the system 100, receiving the patient medical data from the patient medical data interface 120, extracting context specific data from the patient medical data, and initiating one or more medical image viewing subsystems 180 based on the extracted context specific data. Afterwards, the initiated one or more image viewing subsystem 180 is configured for generating a display signal 062 to automatically display a corresponding application interface 60 in the display 80.

The system 100 may be embodied as, or in, a single device or apparatus, such as a mobile device (laptop, tablet, smartphone, etc.), workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system, e.g., the image data interface, the user input interface and the display processor, may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model, e.g., using a server and a thin-client PACS workstation.

Alternatively, the system 100 may be a wearable device used by a patient that is in communicative with a RFID tag attached to the patient or worn by the patient. Alternatively, the wearable device may be a RFID system that includes the RFID tag. For instance, if the RFID tag worn by the patient has "Follow up" attribute, then a previously used image viewing subsystem for viewing the medical image of such patient may be automatically initiated based on the information stored in the memory subsystem 190. The RFID system may further have the functionality of triggering an alert. For instance, if the RFID tag has one of the attribute included as "Pregnant", then the RFID system may automatically trigger an alert signal to caution the technologist about switching on an X-ray system.

Figure 2:
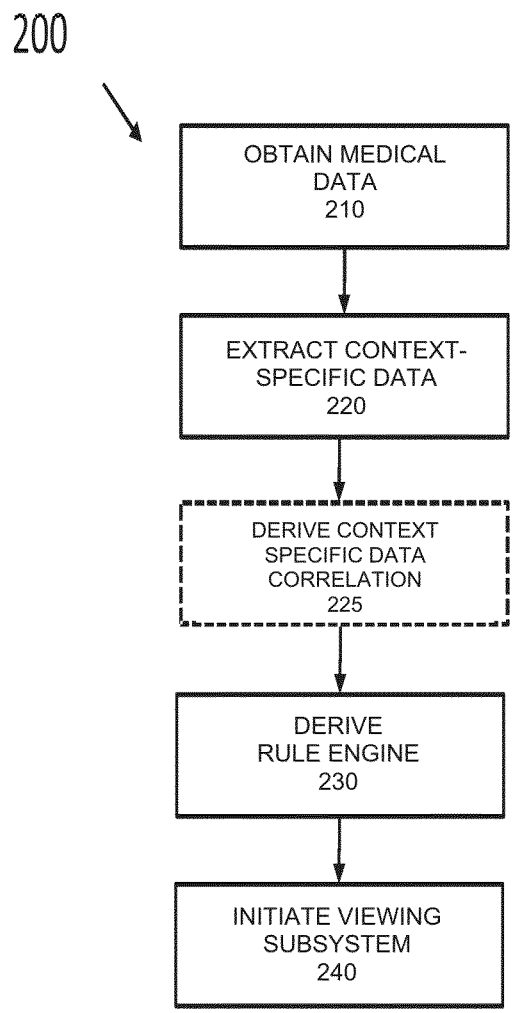
FIG. 2 shows a method for enabling automatically viewing of medical image according to an embodiment of the invention.

FIG. 2 shows a method 200 for enabling a user to automatically viewing image via one or more image viewing subsystems. It is noted that the method 200 may, but does not need to, correspond to an operation of the system 100 as described with reference to FIG. 1.

The method 200 comprises, in an operation titled "OBTAINING MEDICAL DATA OF A PATIENT", obtaining 210 medical data of a patient. The method 200 further comprises, in an operation titled "EXTRACTING CONTEXT SPECIFIC DATA", extracting 220 context specific data from the patient medical data. The method 200 further comprises, in an operation titled "DERIVING A RULE ENGINE DATABASE", deriving 230 a predefined rule engine database 193 comprising association between the context specific data and one or more image viewing subsystems. The method 200 further comprises, in an operation titled "INITIATING AT LEAST ONE IMAGE VIEWING SUBSYSTEM", initiating 240 at least one image viewing subsystem by comparing the context specific data with the predefined rule engine database. It will be appreciated that the above operation may be performed in any suitable order, e.g., consecutively, simultaneously, or a combination thereof, subject to, where applicable, a particular order being necessitated, e.g., by input/output relations. It is noted that some operations may be optional and therefore can be omitted or modified. It is noted that some further operations may be inserted into the method 200. For instance, an operation titled "DERIVING A CORRELATION OF DIFFERENT TYPES OF CONTEXT SPECIFIC DATA", deriving 225 a correlation of different types of context specific data may be inserted between steps 220 and 230. Consequently, the operation titled "INITIATING AT LEAST ONE IMAGE VIEWING SUBSYSTEM" may be modified by initiating at least one image viewing subsystem based on the correlation of the extracted context specific data.

Figure 3:
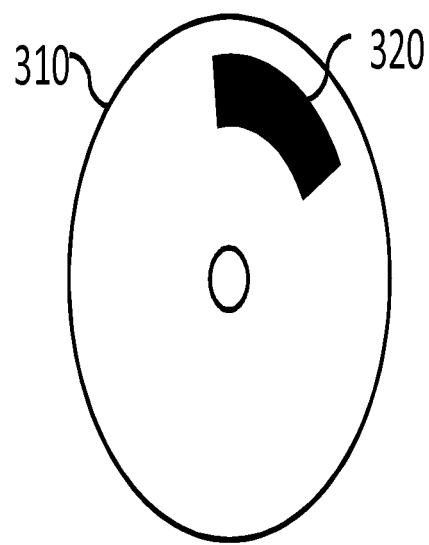
FIG. 3 shows computer readable medium comprising instructions for causing a processor system to perform the method.

The method 200 may be implemented on a computer as a computer implemented method, as dedicated hardware, or as a combination of both. As also illustrated in FIG. 3, instructions for the computer, e.g., executable code, may be stored on a computer readable medium 310, e.g., in the form of a series 320 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 3 shows an optical disc 310. Alternatively, the computer implemented method may be stored in a RFID tag or a RFID system comprising a RFID tag.

Figure 4:
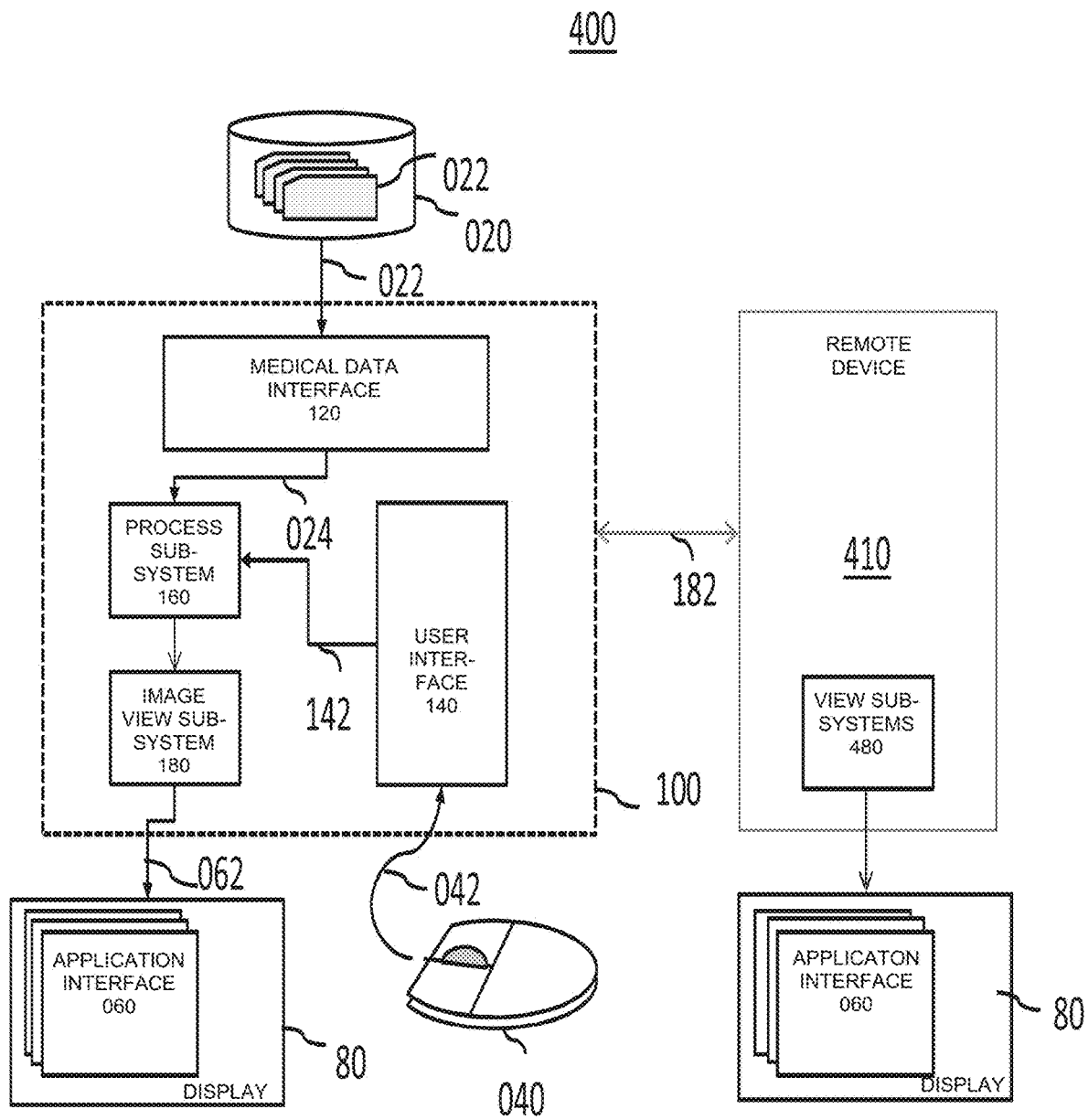
FIG. 4 shows a network system according to an embodiment of the invention.

FIG. 4 schematically depicts a network system 400 comprising a system 100 and one or more remote devices 410 in communicative with the system 100. The remote device 410 may comprise one or more image viewing subsystems 480 which may have the same functionality as the image viewing subsystems 180. The processing subsystem 160 may initiate one or more image viewing subsystems 480 based on the extracted context specific data by transmitting a signal 182 to the remote device 410. The remote device 410 may be either a mobile device, an image acquisition device, or a professional image viewing device, such as Extended Brilliance Workstation™ or Intellispace Portal™.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk, or a RFID tag. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling an automatic medical image viewing workflow, comprising:
   a patient medical data interface for obtaining medical data of a patient; wherein the patient medical data includes:
      a medical image of the patient, and
      audio data associated with the medical image of the patient;
   one or more medical image viewing subsystems;
   a processing subsystem configured to:
      extract context specific data from the obtained patient medical data, and
      initiate at least one image viewing subsystems based on the extracted context specific data,
   wherein the processing subsystem is configured to extract keywords from the audio data inferring the at least one image viewing subsystem to be initiated.

2. The system according to claim 1, wherein the medical data includes a segmented medical image and wherein the processing subsystem is configured to the extract context specific data from the medical image indicating a location of the segmented medical image with respect to a whole body of the patient.

3. The system according to claim 1, wherein the processing subsystem is configured to extract attributes from the medical image protocol inferring the at least one relevant image viewing subsystem to be initiated.

4. The system according to claim 1, wherein the patient medical data includes a medical exam card or medical report and wherein the processing subsystem is configured to extract keywords from the medical exam card or medical report inferring the at least one image viewing subsystem to be initiated.

5. The system according to claim 4, wherein the keywords include:
   a size of a field of view, an organ specific radio-isotope used, or a combination thereof.

6. The system according to claim 1, further comprising
a memory subsystem configured for storing a predefined rule engine database comprising associations between the context specific data and the one or more image viewing subsystems;
wherein the processing subsystem is configured to initiate the at least one medical image viewing subsystem by comparing the context specific data with the predefined rule engine database.

7. The system according to claim 6, wherein the rule engine database further comprises a list of links, wherein each link includes an association between a specific image viewing subsystem and an image acquisition device.

8. The system according to claim 6, further comprising a user input interface for enabling a user to:
provide feedback information to the processing subsystem;
modify the rule engine database;
modify the patient medical data; or
modify a DICOM tag.

9. The system according to claim 6, wherein the processing subsystem is configured to initiate the at least one medical image viewing subsystem based on a correlation of different types of the context specific data.

10. A network comprising:
the system according to claim 1; and
a remote device in communicative with the system, wherein the remote device comprises one or more additional image viewing subsystems, and wherein the processing subsystem is configured to initiate the one or more additional image viewing subsystems based on the extracted context specific data.

11. A system for enabling an automatic medical image viewing workflow, comprising:
a patient medical data interface for obtaining medical data of a patient;
one or more medical image viewing subsystems;
a memory subsystem configured for storing a predefined rule engine database comprising association between context specific data and the one or more image viewing subsystems, and for storing a learn model associated with the initiation of the one or more medical image viewing subsystems to determine whether the initialized one or more image viewing subsystem is applicable to a user of the system, and
a processing subsystem is configured for:
extracting context specific data from the obtained patient medical data;
initiating one or more of the image viewing subsystems based on the extracted context specific data;
receiving feedback information from a user input interface indicating a correctness of the indicated one or more image viewing subsystems with respect to the patient medical data and the extracted context specific data;
updating the rule engine database based on the received feedback information from the user input interface; and
retraining the learn model based on the updated rule engine database using a machine learning process.

12. The system according to claim 11, wherein the patient medical data includes one or more of the following:
a medical image of the patient;
a segmented medical image;
a medical image protocol associated with the medical image of the patient;
a DICOM tag;
audio data associated with the medical image of the patient;
a medical exam card or medical report/record associated with the medical image of the patient.

13. A method of enabling an automatic image viewing workflow, comprising:
obtaining medical data of a patient the medical data including a medical image of the patient and audio data associated with the medical image;
extracting context specific data from the patient medical data including extracting key words from audio data associated with the medical image;
deriving a predefined rule engine database comprising association between the context specific data including the key words and one or more image viewing subsystems;
initiating at least one image viewing subsystem based on the key words extracted from the predefined rule engine database.

14. A non-transitory computer-readable medium carrying instructions to cause a processing subsystem to perform the method according to claim 13.

15. A method of enabling an automatic image viewing workflow, comprising:
storing a predefined rule engine including associations between context-specific data and one or more image viewing subsystems;
storing a learn model associated with an initiation of the one or more medical image viewing systems to determine which of the one or more image viewing systems is applicable to a user;
obtaining medical data of a patient, the medical data including a medical image of the patient;
extracting context-specific data from the patient medical data;
initializing at least one of the one or more image viewing systems based on the extracted context-specific data and the predefined rule engine;
receiving feedback information from a user interface indicating a correctness of the initialized image viewing subsystem with respect to the patient medical data and the extracted context-specific data;
updating the rule engine based on the received feedback information from the user interface; and
retraining the learn model based on the updated rule engine using a machine learning process.

16. A non-transitory computer-readable medium carrying software configured to control a processor to perform the method according to claim 15.

* * * * *